(12) United States Patent
Benner et al.

(10) Patent No.: US 8,216,998 B2
(45) Date of Patent: *Jul. 10, 2012

(54) TREATMENT OF ISCHEMIC EVENTS

(75) Inventors: Robbert Benner, Barendrecht (NL);
Nisar Ahmed Khan, Rotterdam (NL);
Bartholomeus Caspar J. Jacobs,
Rotterdam (NL)

(73) Assignee: Biotempt B.V., Koekange (NL)

( * ) Notice: Subject to any disclaimer, the term of this patent is extended or adjusted under 35 U.S.C. 154(b) by 844 days.

This patent is subject to a terminal disclaimer.

(21) Appl. No.: 11/593,329

(22) Filed: Nov. 6, 2006

(65) Prior Publication Data
US 2007/0054860 A1    Mar. 8, 2007

Related U.S. Application Data

(63) Continuation of application No. 10/409,642, filed on Apr. 8, 2003, now abandoned, which is a continuation-in-part of application No. 10/028,075, filed on Dec. 21, 2001, now abandoned.

(51) Int. Cl.
*A61K 38/00* (2006.01)
*A61K 38/07* (2006.01)
*A61K 38/08* (2006.01)

(52) U.S. Cl. ............ 514/2; 514/2.1; 514/21.8; 514/21.9

(58) Field of Classification Search .................. None
See application file for complete search history.

(56) References Cited

U.S. PATENT DOCUMENTS

| | | |
|---|---|---|
| 3,855,397 A | 12/1974 | Hoffman et al. |
| 3,898,328 A | 8/1975 | Beigler et al. |
| 3,960,830 A | 6/1976 | Bayer et al. |
| 4,003,989 A | 1/1977 | Bar-On |
| 4,083,951 A | 4/1978 | Goudie et al. |
| 4,108,846 A | 8/1978 | Meienhofer |
| 4,140,760 A | 2/1979 | Withington |
| 4,265,874 A | 5/1981 | Bonsen et al. |
| 4,289,750 A | 9/1981 | Kopp et al. |
| 4,330,466 A | 5/1982 | Yanaihara et al. |
| 4,351,762 A | 9/1982 | Verlander et al. |
| 4,427,660 A | 1/1984 | Schiffman et al. |
| 4,571,336 A | 2/1986 | Houck et al. |
| 4,753,965 A | 6/1988 | Stemerick et al. |
| 4,855,285 A | 8/1989 | Stevens |
| 4,966,848 A | 10/1990 | Smith et al. |
| 4,977,244 A | 12/1990 | Muchmore et al. |
| 5,002,961 A | 3/1991 | Dage et al. |
| 5,010,175 A | 4/1991 | Rutter et al. |
| 5,055,447 A | 10/1991 | Palladino et al. |
| 5,070,187 A | 12/1991 | Gavras et al. |
| 5,102,393 A | 4/1992 | Sarnoff et al. |
| 5,175,254 A | 12/1992 | Calas et al. |
| 5,200,507 A | 4/1993 | Chieng |
| 5,223,397 A | 6/1993 | Pouletty |
| 5,223,421 A | 6/1993 | Smith et al. |
| 5,308,834 A | 5/1994 | Scott et al. |
| 5,380,668 A | 1/1995 | Herron |
| 5,436,270 A | 7/1995 | Wang |
| 5,554,378 A | 9/1996 | Uda et al. |
| 5,610,272 A | 3/1997 | Wang |
| 5,616,608 A | 4/1997 | Kinsella et al. |
| 5,677,275 A | 10/1997 | Lunardi-Iskandar et al. |
| 5,700,781 A | 12/1997 | Harris |
| 5,801,193 A | 9/1998 | Ojo-Amaize et al. |
| 5,807,746 A * | 9/1998 | Lin et al. ........................ 435/375 |
| 5,837,218 A | 11/1998 | Peers et al. |
| 5,837,478 A | 11/1998 | Gallatin et al. |
| 5,851,997 A | 12/1998 | Harris |
| 5,854,004 A | 12/1998 | Czernilofsky et al. |
| 5,856,440 A | 1/1999 | Wang |
| 5,858,375 A | 1/1999 | Furminger et al. |
| 5,877,148 A | 3/1999 | Lunardi-Iskandar et al. |
| 5,942,494 A | 8/1999 | Ginsberg et al. |
| 5,958,413 A | 9/1999 | Anagnostopulos et al. |
| 5,966,712 A | 10/1999 | Sabatini et al. |
| 5,968,513 A | 10/1999 | Gallo et al. |
| 5,972,924 A | 10/1999 | Keep et al. |
| 5,981,486 A | 11/1999 | Matsushima et al. |
| 5,994,126 A | 11/1999 | Steinman et al. |
| 5,997,871 A | 12/1999 | Gallo et al. |
| 6,022,696 A | 2/2000 | Harding et al. |
| 6,051,596 A | 4/2000 | Badger |
| 6,075,150 A | 6/2000 | Wang et al. |

(Continued)

FOREIGN PATENT DOCUMENTS

EP          0 572 688          5/1997

(Continued)

OTHER PUBLICATIONS

Kato et al. Reduced hepatic ischemia/reperfusion injury by IL-4: potential anti-inflammatory role of STAT6. Inflammation Research, vol. 49, No. 6, pp. 275-279, Jun. 2000.*

Abeyama et al., A role of NF-κB-dependent gene transactivation in sunburn. The Journal of Clinical Investigation, vol. 105, No. 12, pp. 1751-1759, Jun. 2000.

Abraham, E., Coagulation Abnormalities in Acute Lung Injury and Sepsis, Am. J. Respir. Cell Mol. Biol., 2000, pp. 401-404, vol. 22.

Adib-Conquy et al., NF-κB Expression in Mononuclear Cells in Patients with Sepsis Resembles That Observed in Lipopolysaccharide Tolerance, Am. J. Respir. Crit. Care Med., 2000, pp. 1877-1883, vol. 162.

Agawal et al., Acute Renal Failure, American Family Physician, 2000, pp. 2077-2088, vol. 61, corresponding to web version of p. 1-12.

Albini et al., Old drugs as novel angiogenesis inhibitors: Preclinical studies with NAC, hCG, EGCG and somatostatin, Clinical & Experimental Metastasis, 1999, pp. 739, vol. 17.

(Continued)

Primary Examiner — Jennifer Dunston
(74) Attorney, Agent, or Firm — Traskbritt, P.C.

(57) ABSTRACT

The invention relates to the treatment of an ischemic event such as a stroke or myocardial infarction. The invention provides a method for modulating an ischemic event in a subject comprising providing the subject with a gene-regulatory peptide or functional analogue thereof. Furthermore, the invention provides use of an NF-κB-down-regulating peptide or functional analogue thereof for the production of a pharmaceutical composition for the treatment of reperfusion injury occurring after an ischemic event in a subject.

10 Claims, No Drawings

U.S. PATENT DOCUMENTS

| | | | |
|---|---|---|---|
| 6,086,918 A | 7/2000 | Stern et al. | |
| 6,150,500 A | 11/2000 | Salerno | |
| 6,207,145 B1 | 3/2001 | Tovey | |
| 6,211,151 B1 | 4/2001 | Sikiric et al. | |
| 6,235,281 B1 | 5/2001 | Stenzel et al. | |
| 6,271,199 B2 * | 8/2001 | Brand et al. | 514/2 |
| 6,278,794 B1 | 8/2001 | Parekh et al. | |
| 6,309,822 B1 | 10/2001 | Fodor et al. | |
| 6,310,041 B1 | 10/2001 | Haddox et al. | |
| 6,319,504 B1 | 11/2001 | Gallo et al. | |
| 6,329,573 B1 | 12/2001 | Lightfoot et al. | |
| 6,361,992 B1 | 3/2002 | Szkudlinski et al. | |
| 6,379,970 B1 | 4/2002 | Liebler et al. | |
| 6,416,959 B1 | 7/2002 | Giuliano et al. | |
| 6,489,296 B1 | 12/2002 | Grinnell et al. | |
| 6,507,788 B1 | 1/2003 | Camara y Ferrer et al. | |
| 6,518,021 B1 | 2/2003 | Thastrup et al. | |
| 6,539,102 B1 | 3/2003 | Anderson et al. | |
| 6,583,109 B1 | 6/2003 | Gallo et al. | |
| 6,586,403 B1 | 7/2003 | Mathison et al. | |
| 6,596,688 B1 | 7/2003 | Gallo et al. | |
| 6,620,416 B1 | 9/2003 | Gallo et al. | |
| 6,630,138 B2 | 10/2003 | Gerlitz et al. | |
| 6,642,201 B1 | 11/2003 | Khavinson et al. | |
| 6,645,934 B1 | 11/2003 | Rodemann et al. | |
| 6,652,860 B1 | 11/2003 | Singh et al. | |
| 6,699,656 B2 | 3/2004 | Gallo et al. | |
| 6,711,563 B1 | 3/2004 | Koskas | |
| 6,727,227 B1 | 4/2004 | Khavinson | |
| 6,783,757 B2 | 8/2004 | Brudnak | |
| 6,831,057 B2 | 12/2004 | Baldwin et al. | |
| 6,844,315 B2 | 1/2005 | Khan et al. | |
| 6,852,697 B1 | 2/2005 | Mathison et al. | |
| 6,894,028 B2 | 5/2005 | Lipton et al. | |
| 6,921,751 B1 | 7/2005 | Khan et al. | |
| 7,094,760 B2 | 8/2006 | Mathison et al. | |
| 7,135,286 B2 | 11/2006 | Margus et al. | |
| 7,175,679 B2 * | 2/2007 | Khan et al. | 514/2 |
| 7,316,819 B2 | 1/2008 | Grotts et al. | |
| 7,358,330 B2 | 4/2008 | Khan et al. | |
| 7,365,155 B2 | 4/2008 | Khan et al. | |
| 7,368,535 B2 | 5/2008 | Gorczynski et al. | |
| 7,402,322 B2 | 7/2008 | Khan et al. | |
| 7,501,391 B2 * | 3/2009 | Khan et al. | 514/2 |
| 7,517,529 B2 | 4/2009 | Khan et al. | |
| 7,524,820 B1 | 4/2009 | Khan et al. | |
| 7,560,433 B2 | 7/2009 | Khan et al. | |
| 7,576,174 B2 | 8/2009 | Benner et al. | |
| 7,662,776 B2 | 2/2010 | Khan et al. | |
| 7,786,084 B2 | 8/2010 | Benner et al. | |
| 7,795,226 B2 | 9/2010 | Benner et al. | |
| 2002/0041871 A1 | 4/2002 | Brudnak | |
| 2002/0064501 A1 | 5/2002 | Khan et al. | |
| 2002/0147306 A1 | 10/2002 | Lin et al. | |
| 2002/0155106 A1 | 10/2002 | Hammond | |
| 2003/0003545 A1 | 1/2003 | Ebner et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0148955 A1 | 8/2003 | Pluenneke | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1 | 11/2003 | Khan et al. | |
| 2003/0220261 A1 | 11/2003 | Khan et al. | |
| 2003/0224995 A1 | 12/2003 | Khan et al. | |
| 2004/0013661 A1 | 1/2004 | Wensvoort et al. | |
| 2004/0072246 A1 | 4/2004 | Martin et al. | |
| 2004/0208885 A1 | 10/2004 | Khan et al. | |
| 2005/0037430 A1 | 2/2005 | Khan et al. | |
| 2005/0107314 A1 | 5/2005 | Gorczynski et al. | |
| 2005/0119184 A1 | 6/2005 | Khan et al. | |
| 2005/0214943 A1 | 9/2005 | Khan et al. | |
| 2005/0227925 A1 | 10/2005 | Benner et al. | |
| 2006/0111292 A1 | 5/2006 | Khan et al. | |
| 2006/0142205 A1 | 6/2006 | Benner et al. | |
| 2006/0173162 A1 | 8/2006 | Djurup et al. | |
| 2006/0275255 A1 | 12/2006 | Gudkov | |
| 2007/0054860 A1 | 3/2007 | Benner et al. | |
| 2007/0111948 A1 | 5/2007 | Turdiev | |
| 2007/0197447 A1 | 8/2007 | Khan et al. | |
| 2007/0219138 A1 | 9/2007 | Benner et al. | |
| 2008/0027007 A1 | 1/2008 | Benner et al. | |
| 2008/0076714 A1 | 3/2008 | Khan et al. | |
| 2008/0153755 A1 | 6/2008 | Khan et al. | |
| 2008/0171094 A1 | 7/2008 | Benner et al. | |
| 2008/0176243 A1 | 7/2008 | Khan et al. | |
| 2008/0194489 A1 | 8/2008 | Khan et al. | |
| 2008/0242618 A1 | 10/2008 | Khan et al. | |
| 2008/0242837 A1 | 10/2008 | Khan et al. | |
| 2008/0267936 A1 | 10/2008 | Khan et al. | |
| 2008/0267967 A1 | 10/2008 | Gorczynski et al. | |
| 2008/0306009 A1 | 12/2008 | Khan et al. | |
| 2009/0042807 A1 | 2/2009 | Khan et al. | |
| 2009/0093398 A1 | 4/2009 | Bollekens et al. | |
| 2009/0227505 A1 | 9/2009 | Khan et al. | |
| 2009/0281033 A1 | 11/2009 | Benner et al. | |
| 2009/0291901 A1 | 11/2009 | Benner et al. | |
| 2010/0004172 A1 | 1/2010 | Khan et al. | |
| 2010/0297258 A1 | 11/2010 | Benner et al. | |
| 2011/0009344 A1 | 1/2011 | Benner et al. | |
| 2011/0105415 A1 | 5/2011 | Khan et al. | |
| 2011/0113053 A1 | 5/2011 | Khan et al. | |

FOREIGN PATENT DOCUMENTS

| | | |
|---|---|---|
| EP | 1 138 692 A1 | 10/2001 |
| EP | 1 300 418 | 4/2003 |
| EP | 1 224 212 B1 | 7/2003 |
| EP | 1 466 612 A1 | 10/2004 |
| GB | 2 194 886 A | 3/1988 |
| JP | 09-176187 A | 7/1997 |
| JP | 2003516931 | 5/2003 |
| MO | WO 01/11048 A2 | 2/2001 |
| WO | WO 80/02459 | 11/1980 |
| WO | WO 92/20795 A1 | 11/1992 |
| WO | WO 96/04008 | 2/1996 |
| WO | WO 96/33218 | 10/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 98/06742 | 2/1998 |
| WO | WO 98/34631 A1 | 8/1998 |
| WO | WO 98/35691 | 8/1998 |
| WO | WO 99/31227 | 6/1999 |
| WO | WO 99/59617 | 11/1999 |
| WO | WO 00/17348 | 3/2000 |
| WO | WO 01/10907 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 02/092781 A2 | 11/2002 |
| WO | WO 03/029292 A2 | 4/2003 |
| WO | WO 2004 093897 | 11/2004 |
| WO | WO 2005/011723 A1 | 2/2005 |
| WO | WO 2005/097163 | 10/2005 |
| WO | WO 2006/069198 | 6/2006 |
| WO | WO2009/126037 A1 | 10/2009 |

OTHER PUBLICATIONS

Arima et al., IL-2-Induced Growth of CD8+ T Cell Prolymphocytic Leukemia Cells Mediated by NF-kappaB Induction and IL-2 Receptor alpha Expression, Leukemia Research, 1998, pp. 265-273, vol. 22, No. 3.

Baeuerle et al., Function and Activation of NF-κB in the Immune System, Annu. Rev. Immunol., 1994, pp. 141-179, vol. 12.

Barton et al., Protective Role of Interleukin 6 in the Lipopolysaccharide-Galactosamine Septic Shock Model, Infection and Immunity, Apr. 1993, pp. 1496-1499, vol. 61, No. 4.

Bastin et al., Salt Selection and Optimisation Procedures for Pharmaceutical new Chemical Entities, Org. Proc. Res. Develop. 2000, pp. 427-435, vol. 4.

Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.

Bethea et al., Traumatic Spinal Cord Injury Induces Nuclear Factor-κB Activation, The Journal of Neuroscience, May 1, 1998, pp. 3251-3260, vol. 18, No. 9.

Blackwell et al., The Role of Nuclear Factor-κB in Cytokine Gene Regulation, Am. J. Respir. Cell Mol. Biol., 1997, pp. 3-9, vol. 17.

Bodfish et al., Treating the Core Features of Autism: Are We There Yet? Mental Retardation and Developmental Disabilities Research Reviews, 2004, pp. 318-326, vol. 10.

Borchardt, RT, Optimizing oral absorption of peptides using prodrug strategies, Journal of Controlled Release, Nov. 1999, pp. 231-238, vol. 62.

Bradham et al., Activation of nuclear factor- κB during orthotopic liver transplantation in rats is protective and does not require Kuppfer cells, Liver Transplantation and Surgery, Jul. 1999, pp. 282-293, vol. 5, No. 4.

Brown et al., Two Forms of NF-kappaB1 (p105/p50) in Murine Macrophages: Differential Regulation by Lipopolysaccharide, Interleukin-2, and Interferon-gamma, Journal of Interferon and Cytokine Research, 1997, pp. 295-306. vol. 17.

Burdelya et al., An agonist of toll-like receptor 5 has radioprotective activity in mouse and primate models. Abstract, Science, Apr. 11, 2008, pp. 226-230, vol. 320, No. 5873.

Capizzi, Investigational New Drugs, 1996, 14:249-256.

Christman et al., Nuclear factor kappaB: a pivotal role in the systemic inflammatory response syndrome and new target for therapy, Intens Care Med, 1998, pp. 1131-1138, vol. 24.

Clerici et al., Single-cell analysis of cytokine production shows different immune profiles in multiple sclerosis patients with active or quiescent disease. Journal of Neuroimmunology, vol. 121, pp. 33-101, 2001.

Cleveland BioLabs, Inc., Radiation Antidote for Defense, (visited Apr. 16, 2008) <http://www.cbiolabs.com/Applications.php.

Cohen, Int J. Radiat. Oncol. Biol. Phys., 1987, pp. 251-258, vol. 13.

Connelly et al., Biphasic Regulation of NF-κB Activity Underlies the Pro- and Anti-inflammatory Actions of Nitric Oxide, The Journal of Immunology, 2001, pp. 3873-3881, 166, The American Association of Immunologists, USA.

Cook et al., Modified total lymphoid irradiation and low dose coricosteroids in progressive multiple sclerosis, Journal of Neurological Sciences, vol. 152, pp. 172-181, 1997.

Corvino et al., Availability, stability and sterility of pralidoxime for mass casualty use, Abstract, Ann Emerg Med., Mar. 2006, pp. 272-277, vol. 47, No. 3.

De Saizieu et al., Journal of Bacteriology, vol. 182, No. 17, pp. 4696-4703, Sep. 2000.

Dechend et al., Oncogene, vol. 18, pp. 3316-3323, 1999.

Eckardt et al., Hypoxia-induced accumulation of erythropoietin mRNA in isolated hepatocytes is inhibited by protein kinase C, Pflugers Archiv., 1994, pp. 21-30, vol. 426, Abstract only.

Emmel et al., Cyclosporin A Specifically Inhibits Function of Nuclear Proteins Involved in T Cell Activation, Science, Dec. 22, 1989, pp. 1617-1620, vol. 246.

Epinat et al., Diverse agents act at multiple levels to inhibit the Rel/NF-kappaB signal transduction pathway, Oncogene, 1999, pp. 6896-6909, vol. 18.

Fassio et al., Transforming Growth Factor Alpha and Its Receptor in Neural Retina, Investigative Ophthalmology & Visual Science, Sep. 1989, pp. 1916-1922. vol. 30, No. 9.

Faust et al., Disseminated intravascular coagulation and purpura fulminans secondary to infection, Bailliere's Clinical Haematology, 2000, 179-197, vol. 13. No. 2.

Flores et al., NFkappaB and AP-1 DNA binding activity in patients with multiple sclerosis. J. Neuroimmunol. vol. 135, No. 1-2, pp. 141-147, Feb. 2003.

Friedlander, Tackling anthrax, Nature, Nov. 8, 2001, pp. 160-161, vol. 414.

Garkavtsev et al., Suppression of the novel growth inhibitor p33ING1 promotes neoplastic transformation, Nature Publishing Group, Dec. 14, 1996, pp. 415-420.

Garkavtsev et al., The candidate tumour suppressor p33ING1 cooperates with p53 in cell growth control, Nature, Jan. 15, 1998, pp. 295-298, vol. 391.

GenBank Accession No. NP_000728, GI: 4502789, publicly available Apr. 2007.

Gould, Salt selection for basic drugs, Int. J. Pharm., 1986, pp. 201-217, vol. 33.

Gudkov et al., The role of p53 in determining sensitivity to radiotherapy, Nature Reviews, Feb. 2003, pp. 117-129, vol. 3.

Gudkov, Andrei V., Cancer drug discovery: the wisdom of imprecision, Nature Medicine, Dec. 2004, 1298-00, vol. 10, No. 12.

Gudkov, Andrei V., Converting p53 from a killer into a healer, Nature Medicine, Nov. 2002, pp. 1196-1198, vol. 8. No. 11.

Han et al., Cholecystokinin induction of mob-l chemokine expression in pancreatic acinar cells requires NF-kappaB activation, American Journal of Physiology, Jul. 1999, vol. 277, pp. C74-C82.

http://www.rxlist.com/cgi/generic/chorionic.htm—RX List.com entry for hCG/Pregnyl, printed Jun. 2, 2008.

Hierholzer et al., Essential role of induced nitric oxide in the initiation of the inflammatory response after hemorrhagic shock, J. Exp. Med., Mar. 1998, pp. 917-928, vol. 187, No. 6.

Huang et al., Ischemia-reperfusion and immediate T cell responses, Cellular Immunology, 2007, pp. 4-11, vol. 248.

Husek et al., Rapid screening of urinary proline-hydroxyproline dipeptide in bone turnover studies, Abstract, J. Chromatogr B Analyt Technol Biomed Life Sci., Feb. 5, 2002, pp. 169-174, vol. 767, No. 1.

Ichiyama et al., Systemically administered alpha-melanocyte-stimulating peptides inhibit NF-kappaB activation in experimental brain inflammation, Brain Research, Jul. 1999, pp. 31-37, vol. 836.

Ivanov et al., Hemoglobin as a Source of Endogenous Bioactive Peptides: The Concept of Tissue-Specific Peptide Pool, Biopolymers, 1997, pp. 171-188, vol. 39.

Iyer et al., The transcriptional program in the response of human fibroblasts to serum, Science, Jan. 1999, pp. 83-87, vol. 283, No. 5398.

Jimenez-Garza et al., Early Effects of Modulating Nuclear factor-kappaB Activation on Traumatic Spinal Cord Injury in Rats, Ann. N.Y Acad. Sci., 2005, pp. 148-150, vol. 1053.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kachra et al., Low Molecular Weight Components but Not Dimeric HCG Inhibit Growth and Down-Regulate AP-1 Transcription Factor in Kaposi's Sarcoma Cells, Endocrinology, 1997, pp. 4038-4041, vol. 138, No. 9.

Kanungo et al., Advanced Maturation of *Heteropneustes fossilis* (Bloch) by Oral Administration of Human Chorionic Gonadotropin, J. Adv. Zool., 1999, pp. 1-5, vol. 20.

Kato et al., Reduced hepatic ischemia/reperfusion injury by IL-4: potential anti-inflammatory role of STAT6, Inflammation Research, Jun. 2000, pp. 275-279, vol. 49, No. 6.

Keller et al., Human Chorionic Gonadotropin (hCG) Is a Potent Angiogenic Factor for Uterine Endothelial Cells in Vitro, Placenta, Jul. 1999, pp. A37, vol. 20, No. 5-6.

Khan et al., Inhibition of Diabetes in NOD Mice by Human Pregnancy Factor, Human Immunology, Dec. 2001, pp. 1315-1323, vol. 62, No. 12.

Khan et al., Inhibition of Septic Shock in Mice by an Oligopeptide From the β-Chain of Human Chorionic Gonadotrophin Hormone, Human Immunology, Jan. 2002, pp. 1-7, vol. 63, No. 1.

Khavinson et al, Gerontological Aspects of Genome Peptide Regulation, 2005, S. Karger AG, Basel, Switzerland.

Khavinson et al., Effects of Livagen Peptide on Chromatin Activation in Lymphocytes from Old People, Bulletin of Experimental Biology and Medicine, Oct. 2002, pp. 389-392, vol. 134, No. 4.

Khavinson et al., Effects of Short Peptides on Lymphocyte Chromatin in Senile Subjects, Bulletin of Experimental Biology and Medicine, Jan. 2004, pp. 78-81, vol. 137, No. 1.

Khavinson et al., Epithalon Peptide Induces Telomerase Activity and Telomere Elongation in Human Somatic Cells, Bulletin of Experimental Biology and Medicine, Jun. 2003, pp. 590-592, vol. 135, No. 6.

Khavinson et al., Inductive Activity of Retinal Peptides, Bulletin of Experimental Biology and Medicine, Nov. 2002, pp. 482-484, vol. 134, No. 5.

Khavinson et al., Mechanisms Underlying Geroprotective Effects of Peptides, Bulletin of Experimental Biology and Medicine, Jan. 2002, pp. 1-5, vol. 133, No. 1.

Khavinson et al., Peptide Promotes Overcoming of the Division Limit in Human Somatic Cell, Bulletin of Experimental Biology and Medicine, May 2004, pp. 503-506, vol. 137, No. 5.

Kidd et al., Autism, An Extreme Challenge to Integrative Medicine. Part II: Medical Management, Alternative Medicine Review, 2002, pp. 472-499, vol. 7, No. 6.

Kronfol et al., Cytokines and the Brain: Implications for Clinical Psychiatry, Am. J. Psychiatry, May 2000, pp. 683-694, vol. 157, No. 5.

Lang et al., Induction of apoptosis in Kaposi's sarcoma spindle cell cultures by the subunits of human chorionic gonadtropin, AIDS, 1997, pp. 1333-1340, vol. 11, No. 11.

Li et al., NF-kappaB Regulation in the Immune System, Nature Reviews/Immunology, Oct. 2002, pp. 725-734, vol. 2.

Lin et al., The Journal of Biological Chemistry, vol. 270. No. 24, pp. 14255-14258, Jun. 1995.

Lunardi-Iskandar et al., Effects of a urinary factor from women in early pregnancy on HIV-a, SIV and associated disease, Nature Medicine, Apr. 1998, pp. 428-434, vol. 4, No. 4.

Lutterova et al., Marked difference in tumor necrosis factor-alpha expression in warm ischemia- and cold ischemia-reperfusion of the rat liver, Cryobiology, 2000, pp. 301-314, vol. 41.

Malek-Ahmadi, P., Role of Cytokines in Psychopathology: Therapeutic Implications, Drug News Prospects, Jun. 1998, pp. 271-276, vol. 11, No. 5.

Malyak et al., Characterization of a Low Molecular Weight Isoform of IL-1 Receptor Antagonist, The Journal of Immunology, 1998, pp. 1997-2003, vol. 161.

Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

McBean et al., Rodent Models of Global Cerebral Ischemia: A Comparison of Two-Vessel Occlusion and Four-Vessel Occlusion, Gen. Pharmac., 1998, pp. 431-434, vol. 30. No. 4.

McDonald et al., Interleukin-15 (IL-15) Induces NF-kappaB Activation and IL-8 Production in Human Neutrophils, Blood, Dec. 15, 1998, pp. 4828-4835, vol. 92, No. 12.

MedlinePlus, Medical Encyclopedia: autoimmune disorders (www.nlm.gov/medlineplus/ency/article/000816.htm), printed Jun. 7, 2007.

Medzhitov, Toll-like Receptors and Innate Immunity, Nature Reviews/Immunology, Nov. 2001, pp. 135-145, vol. 1.

Morozov et al., Natural and Synthetic Thymic Peptides as Therapeutics for Immune Dysfunction, Int. J. Immunopharmac., 1997. pp. 501-505, vol. 19, No. 9/10.

Muchmore et al., Immunoregulatory Properties of Fractions from Human Pregnancy Urine: Evidence that Human Chorionic Gonadotropin is not Responsible. The Journal of Immunology, Mar. 1997, pp. 881-886, vol. 118, No. 3.

Muchmore et al., Purification and Characterization of a Mannose-Containing Disaccharide Obtained from Human Pregnancy Urine. Journal of Experimental Medicine, Dec. 1984, pp. 1672-1685, vol. 160.

NCBI Accession No. AAI06724, version Oct. 6, 2006.

Neely et al., Then and now: Studies using a burned mouse model reflect trends in burn research over the past 25 years, Burns, 1999, pp. 603-609, vol. 25.

Ngo et al., The protein folding problem and tertiary structure prediction, 1994, pp. 492-494.

Ohlsson et al., Interleukin-1 Receptor Antagonist Reduces Mortality from Endotoxin Shock, Nature, Dec. 6, 1990, pp. 550-552. vol. 348.

Oka et al., Immunosuppression in organ transplantation, Japanese Journal of Pharmacology, vol. 71, No. 2, pp. 89-100, Jun. 1996.

Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.

Padmos et al., A discriminating messenger RNA signature for bipolar disorder formed by an aberrant expression of inflammatory genes in monocytes, Arch Gen Psychiatry, Apr. 2008, pp. 395-407, vol. 65, No. 4.

Pan et al., Bradykinin Stimulates NF-κB Activation and Interleukin 1β Gene Expression in Cultured Human Fibroblasts, J. Clin. Invest., Nov. 1996, pp. 2042-2049, vol. 98, No. 9, The American Society for Clinical Investigation, Inc.

Partial European Search Report for 02 763 111.8 dated Nov. 23, 2007.

Patil et al., The Study of the Effect of Human Chorionic Gonadotrophic (HCG) Hormone on the Survival of Adrenal Medulla Transplant in Brain. Preliminary Study, ACTA Neurochir (Wien), 1987, pp. 76-78, vol. 87.

PCT International Search Report and Written Opinion, PCT/NL2007/050092, dated Jul. 6, 2007.

PCT International Search Report, International Application No. PCT/NL02/00639, mailed Aug. 4, 2003.

PCT International Search Report, PCT/CA97/00568, dated Apr. 30, 1998.

PCT International Search Report, PCT/EP2005/003707, dated Jul. 5, 2005.

Qin et al., Nuclear Factor kB Nuclear Translocation Upregulates c-Myc and p53 Expression during NMDA Receptor-Mediated Apoptosis in Rat Striatum, The Journal of Neuroscience, May 15, 1999, pp. 4023-4033, vol. 19, No. 10.

Quillan et al., Combinatorial diffusion assay used to identify topically active melanocyte-stimulating hormone receptor antagonists, PNAS, Mar. 1995, pp. 2894-2898, vol. 92, USA.

"RDT&E Budget item justification sheet" StartDateMarker 1999, EndDateMarker Retrieved from the Internet: URL:http://www.dtic.mil/descriptivesum/Y2000/OSD/PE0602787D.pdf>.

Redon et al., Global variation in number in the human genome, Nature, Nov. 23, 2006, pp. 444-454, vol. 444.

Rodriguez et al., Expression of human HLA-B27 transgene alters susceptibility to murine theiler's virus-induced demylenination, 1991, vol. 146, pp. 2596-2602.

Rohrig et al., Growth-stimulating Influence of Human Chorionic Gonadotropin (hCG) on *Plasmodium falciparum* in vitro, Zentralblatt Bakt, 1999, pp. 89-99, vol. 289.

Samaniego et al., Induction of Programmed Cell Death in Kaposi's Sarcoma Cells by Preparations of Human Chorionic Gonadotropin, Journal of the National Cancer Institute, Jan. 20, 1999, pp. 135-143, vol. 91. No. 2.

Sharma, Septic Shock, (visited Sep. 27, 2007 <http://www.emedicine.com/MED/topic2101.htm>, pp. 1/28-27/28.

Slater et al., Decreased Mortality of Murine Graft-Versus-Host Disease by Human Chorionic gonadotropin, Transplantation, Jan. 1977, pp. 103-104, vol. 23, No. 1.

Smith et al., Recent developments in drug therapy for multiple sclerosis, Multiple Sclerosis, 1999, pp. 110-120, vol. 5.

Sovak et al., Aberrant nuclear factor-kappa B/Rel expression and the pathogenesis of breast cancer, The Journal of Clinical Investigation, Dec. 1997, pp. 2952-2960, vol. 100, No. 12.

Strom et al., Small-molecule inhibitor of p53 binding to mitochondria protects mice from gamma radiation, Nature Chemical Biology, Sep. 2006, pp. 474-479, vol. 2, No. 9.

Szinicz, L., History of chemical and biological warfare agents, Abstract, Toxicology, Oct. 30, 2005, pp. 167-181, vol. 214, No. 3.

Tak et al., NF-kappaB: a key role in inflammatory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Thibonnier et al., Cytoplasmic and nuclear signaling pathways of V1-vascular vasopressin receptors, Regulatory Peptides, 1993, pp. 79-84, vol. 45.

Tovey et al., Mucosal Cytokine Therapy: Marked Antiviral and Antitumor Activity, J. Interferon Cytokine Res., 1999, pp. 911-921, vol. 19.

Traystman, R., Animal Models of Focal and Global Cerebral Ischemia, ILAR Journal, 2003, pp. 85-95, vol. 44, No. 2.

Valore et al., Human b-Defensin-1: An antimicrobial Peptide of Urogenital Tissues, J. Clin. Invest., Apr. 1998, pp. 1633-1642, vol. 101, No. 8.

Wallraff et al., Urinary Excretion of Amino Acids in Pregnancy, J. Clinc. Invest., 1950, pp. 1542-1544, vol. 29.

Weinberger et al., Mechanisms Mediating the Biologic Activity of Synthetic Proline, Glycine, and Hydroxyproline Polypeptides in Human Neurophils, Mediators of Inflammation, 2005, pp. 31-38, vol. 1.

Wu et al., Gonadotropin-Releasing Hormone (GNRH) Cleavage Products are Involved in the Regulation of GNRH Gene Expression in the GTI-7 Neuronal Cell Line, Society for Neuroscience Abstracts. Nov. 4, 2000, pp. 7.8, XP009091566, vol. 26, No. 1-2.

Wulczyn et al., The NF-κB/Rel and IkB gene families: mediators of immune response and inflammation, J. Mol. Med., 1996, pp. 749-769, vol. 74, No. 12.

Yamamoto et al., Role of the NF-κB Pathway in the Pathogenesis of Human Disease States, Current Molecular Medicine, Jul. 2001, pp. 287-296, vol. 1, No. 3.

Yang et al., Increased cortical nuclear factor κB (NF-κB) DNA binding activity after traumatic brain injury in rats, Neuroscience Letters, 1995, pp. 101-104, vol. 197.

Zhou et al., Transplantation tolerance in NF-κB-impaired mice is not due to regulation but is prevented by transgenic expression of Bcl-xL. The Journal of Immunology. vol. 174, No. 6. pp. 3447-3453, Mar. 2005.

Office Action for U.S. Appl. No. 10/409,032 dated May 17, 2007.
Office Action for U.S. Appl. No. 10/409,032 dated Jan. 15, 2008.
Office Action for U.S. Appl. No. 10/409,032 dated Aug. 20, 2008.
Office Action for U.S. Appl. No. 10/409,032 dated Jun. 1, 2009.
Office Action for U.S. Appl. No. 11/037,972 dated Oct. 11, 2007.
Office Action for U.S. Appl. No. 11/037,972 dated Jun. 4, 2008.
Office Action for U.S. Appl. No. 11/037,972 dated Dec. 12, 2008.
Office Action for U.S. Appl. No. 11/446,458 dated Jun. 15, 2007.
Office Action for U.S. Appl. No. 11/446,458 dated Jan. 11, 2008.
Office Action for U.S. Appl. No. 11/446,458 dated Jul. 28, 2008.
Office Action for U.S. Appl. No. 11/446,458 dated Mar. 6, 2009.
Office Action for U.S. Appl. No. 11/593,329 dated Apr. 6, 2009.
Office Action for U.S. Appl. No. 11/715,314 dated Feb. 26, 2009.
Office Action for U.S. Appl. No. 11/715,314 dated Aug. 14, 2009.
Office Action for U.S. Appl. No. 11/975,284 dated Dec. 29, 2008.
Office Action for U.S. Appl. No. 11/975,284 dated Oct. 1, 2009.
Office Action for U.S. Appl. No. 11/982,292 dated May 18, 2009.
Office Action for U.S. Appl. No. 11/982,292 dated Aug. 28, 2009.

U.S. Appl. No. 10/409,032, filed Apr. 8, 2003, Inventor: Benner et al., Title: Treatment of Trauma.
U.S. Appl. No. 11/037,972, filed Jan. 18, 2005, Inventor: Khan et al., Title: Immunoregulator.
U.S. Appl. No. 11/446,458, filed Jun. 2, 2006, Inventor: Drexhage et al., Title: Method to Diagnose or Screen for Inflammatory Diseases.
U.S. Appl. No. 11/481,423, filed Jul. 5, 2006, Inventor: Khan et al., Title: Treatment for Tumors.
U.S. Appl. No. 11/600,294, filed Nov. 15, 2006, Inventor: Khan et al., Title: Oligopeptide Acetate and Formulations Thereof.
U.S. Appl. No. 11/715,314, filed Mar. 7, 2007, Inventor: Benner et al., Title: Control of Radiation Injury.
U.S. Appl. No. 11/975,284, filed Oct. 17, 2007, Inventor: Khan et al., Title: Treatment for Tumors.
U.S. Appl. No. 11/981,491, filed Oct. 30, 2007, Inventor: Khan et al., Title: Treatment of Iatrogenic Disease.
U.S. Appl. No. 11/981,505, filed Oct. 30, 2007, Inventor: Benner et al., Title: Treatment of Burns.
U.S. Appl. No. 11/982,292, filed Oct. 31, 2007, Inventor: Khan et al., Title: Treatment of Neurological Disorders.
U.S. Appl. No. 11/982,293, filed Oct. 31, 2007, Inventor: Khan et al., Title: Stratification.
U.S. Appl. No. 11/986,043, filed Oct. 30, 2007, Inventor: Khan et al., Title: Peptide Compositions.
U.S. Appl. No. 12/001,035, filed Dec. 6, 2007, Inventor: Khan et al., Title: Gene Regulator.
U.S. Appl. No. 12/069,401, filed Feb. 8, 2008, Inventor: Khan et al., Title: Immunoregulatory Compositions.
U.S. Appl. No. 12/069,741, filed Feb. 12, 2008, Inventor: Khan et al., Title: Treatment of Trauma-Hemorrhage With Short Oligopeptides.
U.S. Appl. No. 12/083,472, filed Apr. 11, 2008, Inventor: Drexhage et al., Title: Method to Diagnose or Screen for Inflammatory Diseases.
U.S. Appl. No. 12/288,935, filed Oct. 24, 2008, Inventor: Benner et al., Title: Control of Radiation Injury.
U.S. Appl. No. 12/383,849, filed Mar. 27, 2009, Inventor: Khan et al., Title: Compositions for Mucosal and Oral Administration Comprising HCG Fragments.
U.S. Appl. No. 12/386,061, filed Apr. 9, 2009, Inventor: Khan et al., Title: Methods and Uses for Protein Breakdown Products.
U.S. Appl. No. 12/386,135, filed Apr. 14, 2009, Inventor: Khan et al., Title: Gene Regulator.
U.S. Appl. No. 12/460,317, filed Jul. 15, 2009, Inventor: Benner et al., Title: Control of Radiation Injury.

Altuvia et al., A structure-based approach for prediction of MHC-binding peptides, Methods, 2004, pp. 454-459, vol. 34.

Austin et al., C-terminal motif prediction in eukaryotic proteomes using comparative genomics and statistical over-representation across protein families, BMC Genomics, 2007, 8:191.

Kunik et al., Functional Representation of Enzymes by Specific Peptides, PLOS Computational Biology, Aug. 2007, pp. e167; vol. 3, No. 8.

Altavilla, et al., Tumour necrosis factor-α as a target of melanocortins in haemorrhagic shcok, in the anaesthetized rat, British Journal of Pharmacology, 1998, pp. 1587-1590, vol. 24, No. 8.

Audran, M., Iatrogenic Demineralizing osteopathies, Presse Med. Feb. 12, 1994: 23(6); 271-3, Abstract only.

Babu, V.V. Suresh (Synthetic Communications 29(1), 79-91, 1999).

Bardin, et al., Nephrogenic systemic fibrosis, Current Opinion in Rheumatology 2010, 22:54-58.

Chiao, et al., α-Melanocyte-stimulating Hormone Protects Against Renal Injury after Ischenia in Mice and Rats, The Amercian Society for Clincial Investigation, Inc., vol. 99, No. 6; Mar. 1997, 1165-1172.

Hunsinger, et al., Is there a basis for novel pharmacotherapy of autism?, Life Sciences 67 (2000) 1667-1682.

Invernizzi, et al. Osteoporosis in Parkinson's disease, Parkinsonism Relat Disord. Jun. 2009: 15(5); 339-46, Abstract only.

Jensen, et al. Xerostomia and hypofunction of the salivary glands in cancer therapy. Support Care Cancer (2003) 11:207-225.

Kintzel, PE., Anticancer drug-induced kidney disorders. Drug Saf. Jan. 2001; 24(1): 19-38, Abstract only.

Lyons, II, et al., Diabetes Management: Current Diagnostic Criteria, Drug Therapies, and State Legislation: The American Journal of Managed Care vol. 3 No. 10: Oct. 1997; pp. 1599-1612.

Manna, et al., α-Melanocyte-Stimulating Hormone Inhibits the Nuclear Transcription Factor NF-κB Activation Induced by Various Inflammatory Agents, The American Association of The Immunologists, pp. 2873-2880, 1998.

Rizzo et al., Wild-type p53 differentially affects tumorigenic and metastatic potential of murine metastatic cell variants. Clin. Exp. Metastasis. 1993, pp. 368-376, vol. 11.

Roice, M. (Tetrahedron 56(23), 3725-3734, 2000).

Van Holde, Physical Biochemistry. Prentice-Hall, 1971, pp. 39-47.

Waldum, et al., Antiulcer Drugs and Gastric Cancer, Digestive Diseases and Sciences, vol. 50 Supplement I (Oct. 2005); pp. S39-S44.

Will, Robert G. Acquired prion disease: Iatrogenci CJD, variant CJD, kuru, British Medical Bulletin 2003: 66: 255-265.

Yoshida, International Journal of Pharmaceutics, 2007, pp. 142-147, vol. 337, No. 1-2.

Office Action for U.S. Appl. No. 11/446,458 dated Sep. 2, 2008.
Office Action for U.S. Appl. No. 11/481,423 dated Jan. 31, 2008.
Office Action for U.S. Appl. No. 11/481,423 dated Apr. 16, 2009.

Office Action for U.S. Appl. No. 11/481,423 dated Jul. 24, 2008.
Office Action for U.S. Appl. No. 11/593,329 dated Mar. 5, 2010.
Office Action for U.S. Appl. No. 11/600,294 dated Apr. 3, 2009.
Office Action for U.S. Appl. No. 11/600,294 dated Dec. 17, 2009.
Office Action for U.S. Appl. No. 11/981,505 dated May 27, 2009.
Office Action for U.S. Appl. No. 11/981,505 dated Sep. 29, 2009.
Office Action for U.S. Appl. No. 11/986,043 dated Nov. 20, 2009.
Office Action for U.S. Appl. No. 11/986,043 dated Feb. 18, 2010.
Notice of Allowance for U.S. Appl. No. 11/715,314 dated Apr. 12, 2010.
Notice of Allowance for U.S. Appl. No. 11/981,505 dated Mar. 25, 2010.
Burdelya et al., NF-kappaB activating proteins as radioprotectants: Derivatives of Flagellin from *Salmonella* protect mice from hematopoietic and gastrointestinal Radiation Syndromes, Cleveland Biolabs, Inc., International Workshop in Space Radiation Research 2004.
Cui et al., Am. J. Physiol. Integr. Comp. Physiol., 2004, pp. R699-R709, vol. 286.
Daemen et al., Ischemia-reperfusion-induced IFN-gamma up-regulation: involvement of IL-12 and IL-13, The Journal of Immunology, 1999, pp. 5506-5510, vol. 162.
Dietrich et al., Postischemic hypothermia and IL-10 treatment provide long-lasting neuroprotection of CA1 hippocampus following transient global ischemia in rats. Experimental Neurology, 1999, pp. 444-450, vol. 158.
Donnahoo et al., Early kidney TNF-alpha expression mediates neutrophil infiltration and injury after renal ischemia-reperfusion, American Journal of Physiology, Sep. 1999, pp. R922-R929, vol. 277, No. 3, Pt. 2.
Dwinnell et al., Atlas of Diseases of the Kidney, Blackwell Sciences, 1999, pp. 12.1-12.12, Ch. 12.
Engles et al., Exogenous human recombinant interleukin-10 attenuates hindlimb ischemia-reperfusion injury, Journal of Surgical Research, 1997, pp. 425-428, vol. 69.
Kalns et al., Biochem. Biophys. Res. Comm., 2002, pp. 41-44, vol. 292.
Kalns et al., Biochem. Biophys. Res. Comm., 2002, pp. 506-509, vol. 297.
Keeton and Gould, Biological Science, 5th Ed., New York, W.W. Norton & Company, Inc. 1993, p. 4.
Endo et al., Plasma endotoxin and cytokine concentrations in patients with hemorrhagic shock, Crit Care Med, 1994, pp. 949-955, vol. 22L.
Hummel et al., Topical and Systemic Antibacterial Agents in the Treatment of Burns, Annals Surg., 1970, pp. 370-384, vol. 173, No. 3.
Lane et al., Interleukin-10 reduces the systemic inflammatory response in a murine model of intestinal ischemia/reperfusion, Surgery, 1997, pp. 288-294, vol. 122, No. 2.
Le Moine et al., Cold liver ischemia-reperfusion injury critically depends on liver T cells and is improved by donor pretreatment with interleukin 10 in mice, Hepatology, 2000, pp. 1266-1274, vol. 31, No. 6.
Lider et al., Suppression of Experimental Autoimmune Diseases and Prolongation of Allograft Survival by Treatment of Animals with Low Doses of Heparin, J. Clin. Invest., 1989, pp. 752-756, vol. 83.
Merck Index, 17th ed. 1999, pp. 1145-1146, 1841-1848, 2539, 2551.
Merriam-Webster Medical Dictionary, 1994, p. 82.
Moayeri et al., Journal of Clinical Investigation, Sep. 2003, pp. 670-682, vol. 112, No. 5.
Molina et al., Central Sympathetic Modulation of Tissue Cytokine Response to Hemorrhage, Neuroimmunomodulation, 1999, pp. 193-200, vol. 6.
Morales et al., Reversal by Vasopressin of Intractable Hypotension in the Late Phase of Hemorrhage Shock, Circulation, 1999, pp. 226-229, vol. 100.
PCT International Search Report, PCT/NL01/00259, dated Dec. 18, 2001.
Pellizzari et al., FEBS Letters, 1999, pp. 199-204, vol. 462.
Riera et al., Neutrophils accentuate renal cold ischemia-reperfusion injury. Dose-dependent protective effect of platelet-activating factor receptor antagonist, The Journal of Pharmacology and Experimental Therapeutics, 1997, pp. 786-794, vol. 280, No. 2.
Saavedra et al., Targeting Nitric Oxide Delivery in Vivo, J. Medicinal Chemistry, Jun. 20, 1997, pp. 1947-1954, vol. 40, No. 13.
Selzman et al., Interleukin-10 inhibits postinjury tumor necrosis factor-mediated human vascular smooth muscle proliferation, Journal of Surgical Research, 1998, pp. 352-356, vol. 80.

* cited by examiner

```
                        SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gln Gly Val
 1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Gly Val
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Gly Ala
 1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Pro Ala Leu Pro
 1               5

<210> SEQ ID NO 5
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Pro Ala Leu Pro
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala Pro Ala Leu Pro
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Pro Ala Leu Pro Gln
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Pro Ala Ala Pro Gln
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Pro Ala Leu Ala Gln
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ala Gly Val
  1
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Ala Ala Leu Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Pro Ala Leu Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Pro Ala Leu Pro Gln
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Leu Ala Ala Leu Pro Gln
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Leu Pro Ala Leu Pro Ala
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Gly Val Leu Pro Ala Leu Pro
  1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Gly Val Leu Pro Ala Leu Pro Gln Val Val Cys
  1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Gly Cys Pro Arg Gly Val Asn Pro Val Val Ser
  1               5                  10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Gly Cys
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Thr Arg Val
  1

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Ala Leu Pro Gln Val Val Cys
  1               5                  10

<210> SEQ ID NO 22
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Leu Gln Gly Val Leu Pro Ala Leu Pro Gln
 1               5                  10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Leu Pro Ala Leu Pro Gln
 1               5

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
                20                  25                  30

Ser Cys Gln Cys Ala Leu
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Arg Cys Arg Pro Ile Asn Ala Thr Leu Ala Val Glu Lys Glu
 1               5                  10                  15

Gly Cys Pro Val Cys Ile Thr Val Asn Thr Thr Ile Cys Ala Gly Tyr
                20                  25                  30

Cys Pro Thr
        35

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Lys Ala Pro Pro Pro Ser Leu Pro Ser Pro Ser Arg Leu Pro Gly
 1               5                  10                  15

Pro Ser
```

```
<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Arg Leu Pro Gly Cys Pro Arg Gly Val Asn Pro Val Val Ser
  1               5                  10                  15

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agctcagagg gggactttcc gagag                                              25

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Val Cys
  1
```

TREATMENT OF ISCHEMIC EVENTS

CROSS-REFERENCE TO RELATED APPLICATIONS

This application is a continuation of U.S. patent application Ser. No. 10/409,642, filed Apr. 8, 2003, which is a continuation-in-part of U.S. patent application Ser. No. 10/028,075, filed Dec. 21, 2001. The contents of U.S. Ser. No. 10/409,642, filed Apr. 8, 2003, U.S. Ser. No. 10/028,075, filed Dec. 21, 2001, and U.S. Ser. No. 10/262,522, filed Sep. 30, 2002, are incorporated herein by this reference.

TECHNICAL FIELD

The current invention relates to the body's innate way of modulating important physiological processes and builds on insights reported in PCT International Publications WO99/59617 and WO01/72831 and PCT International Application PCT/NL02/00639, the contents of the entirety of all of which are incorporated herein by this reference.

BACKGROUND

In the aforementioned applications, small gene-regulatory peptides are described that are present naturally in pregnant women and are derived from proteolytic breakdown of placental gonadotropins such as human chorionic gonadotropin (hCG) produced during pregnancy. These peptides (in their active state often only at about 4 to 6 amino acids long) were shown to have unsurpassed immunological activity that they exert by regulating expression of genes encoding inflammatory mediators such as cytokines. Surprisingly, it was found that breakdown of hCG provides a cascade of peptides that helps maintain a pregnant woman's immunological homeostasis. These peptides are nature's own substances that balance the immune system to assure that the mother stays immunologically sound while her fetus does not get prematurely rejected during pregnancy but instead is safely carried until its time of birth.

Where it was generally thought that the smallest breakdown products of proteins have no specific biological function on their own (except to serve as antigen for the immune system), it now emerges that the body, in fact, routinely utilizes the normal process of proteolytic breakdown of the proteins it produces to generate important gene-regulatory compounds, short peptides that control the expression of the body's own genes. Apparently, the body uses a gene-control system ruled by small, broken-down products of the exact proteins that are encoded by its own genes.

It is known that, during pregnancy, the maternal system introduces a status of temporary immunomodulation which results in suppression of maternal rejection responses directed against the fetus. Paradoxically, during pregnancy, often the mother's resistance to infection is increased and she is found to be better protected against the clinical symptoms of various autoimmune diseases such as rheumatism and multiple sclerosis. The protection of the fetus thus cannot be interpreted as only a result of immune suppression. Each of the above three applications has provided insights by which the immunological balance between protection of the mother and protection of the fetus can be understood.

It was shown that certain short breakdown products of hCG (i.e., short peptides which can easily be synthesized, if needed modified, and used as a pharmaceutical composition) exert a major regulatory activity on pro- or anti-inflammatory cytokine cascades that are governed by a family of crucial transcription factors, the NF-κB family, which stands central in regulating the expression of genes that shape the body's immune response.

Most of the hCG produced during pregnancy is produced by cells of the placenta, the exact organ where cells and tissues of mother and child most intensely meet and where immunomodulation is most needed to fight off rejection. Being produced locally, the gene-regulatory peptides which are broken down from hCG in the placenta immediately balance the pro- or anti-inflammatory cytokine cascades found in the no-man's land between mother and child. Being produced by the typical placental cell, the trophoblast, the peptides traverse extracellular space, enter cells of the immune system and exert their immunomodulatory activity by modulating NF-κB-mediated expression of cytokine genes, thereby keeping the immunological responses in the placenta at bay.

BRIEF SUMMARY OF THE INVENTION

It is postulated herein that the beneficial effects seen on the occurrence and severity of autoimmune disease in the pregnant woman result from an overspill of the hCG-derived peptides into the body as a whole; however, these effects must not be overestimated, as it is easily understood that the further away from the placenta, the less immunomodulatory activity aimed at preventing rejection of the fetus will be seen, if only because of a dilution of the placenta-produced peptides throughout the body as a whole. However, the immunomodulatory and gene-regulatory activity of the peptides should by no means only be thought to occur during pregnancy and in the placenta; men and women alike produce hCG, for example, in their pituitaries, and nature certainly utilizes the gene-regulatory activities of peptides in a larger whole.

Consequently, a novel therapeutic inroad is provided, using the pharmaceutical potential of gene-regulatory peptides and derivatives thereof. Indeed, evidence of specific up- or down-regulation of NF-κB-driven pro- or anti-inflammatory cytokine cascades that are each, and in concert, directing the body's immune response was found in silico in gene arrays by expression profiling studies, in vitro after treatment of immune cells and in vivo in experimental animals treated with gene-regulatory peptides. Also, considering that NF-κB is a primary effector of disease (A. S. Baldwin, J. Clin. Invest., 2001, 107:3-6), using the hCG-derived gene-regulatory peptides offers significant potential for the treatment of a variety of human and animal diseases, thereby tapping into the pharmaceutical potential of the exact substances that help balance the mother's immune system such that her pregnancy is safely maintained.

DETAILED DESCRIPTION OF THE INVENTION

The invention in particular relates to the treatment of an ischemic event such as a stroke or myocardial infarction.

An ischemic event refers to an event in which the blood supply to a tissue is obstructed. Due to this obstruction, the endothelial tissue lining the affected blood vessels becomes "sticky" and begins to attract circulating white blood cells. The white cells bound to the endothelium eventually migrate into the affected tissue, causing significant tissue destruction. Although neither acute myocardial infarction nor stroke is directly caused by inflammation, much of the underlying pathology and the damage that occurs after an acute ischemic event are caused by acute inflammatory responses during reperfusion, the restoration of blood flow to the affected organ. Early restitution of blood flow to ischemic tissues is essential to halt the progression of cellular injury associated with decrease of oxygen supply and nutrient delivery. This fact provides the basis for the traditional view that minimizing ischemic time is the only important intervention for diminishing the extent of ischemic injury. However, it is now well recognized that reperfusion of ischemic tissues initiates a complex series of reactions that can paradoxically injure tissues. Although several mechanisms have been proposed to explain the pathogenesis of ischemia—reperfusion injury, most attention has focused on a role for reactive oxygen and nitrogen metabolites and inflammatory leukocytes. In addition to the local tissue injury, distant organs can also be affected, particularly if the intensity of the inflammatory reaction in post-ischemic tissue (e.g., intestine) is great. The remote effects of ischemia—reperfusion injury are most frequently observed in the lung and (cardio- or cerebro-)vascular system, and can result in the development of the systemic inflammatory response syndrome (SIRS) and multiple organ dysfunction syndrome (MODS), both of which account for 30-40% of the mortality in tertiary referral intensive care units (ICUs). This application, however, mostly deals with localized ischemic events.

In PCT International Publication WO 01/72831, a method and a pharmaceutical composition are provided for modulating cardiovascular or circulatory disorders, such as heart failure, brain infarctions, Alzheimer's disease, thrombosis, arteriosclerosis, pregnancy-related cardiovascular or circulatory disorders and the like. It has been found that an immunoregulator as described in the application has a very beneficial effect on animals, including humans, suffering from a cardiovascular disorder. The immunoregulator according to PCT International Publication WO 01/72831 also widens the scope of possibilities of dotter treatments. In cases where conventionally such a treatment could not be performed because of risks of an oxygen tension becoming too low, a dotter treatment in cases of myocardial infarction is feasible when combined with treatment with the immunoregulator. Accordingly, expensive and difficult bypass surgery may, in many cases, be avoided, and the application also suggested the same protective effect of the immunoregulator in other organs as well in circulatory-related disease.

The current invention provides additional modes and means of treatment. The invention provides a method for modulating an ischemic event in a subject believed to be in need thereof comprising providing the subject with a signaling molecule comprising a short gene-regulatory peptide or functional analogue thereof, wherein the signaling molecule is administered in an amount sufficient to modulate the ischemic event. The signal molecule is preferably a short peptide, preferably of at most 30 amino acids long, or a functional analogue or derivative thereof. In a much preferred embodiment, the peptide is an oligopeptide of from about 3 to about 15 amino acids long, preferably 4 to 12, more preferably 4 to 9, most preferably 4 to 6 amino acids long, or a functional analogue or derivative thereof. Of course, such signaling molecule can be longer, for example, by extending it (N- and/or C-terminally) with more amino acids or other side groups, which can, for example, be (enzymatically) cleaved off when the molecule enters the place of final destination. In particular, a method is provided wherein the signaling molecule modulates translocation and/or activity of a gene transcription factor. It is particularly useful when the gene transcription factor comprises an NF-κB/Rel protein or an AP-1 protein. Ischemia induces increased expression of inflammatory cytokines due to activation of NF-κB and AP-1, and in a preferred embodiment, the invention provides a method wherein translocation and/or activity of the NF-κB/Rel protein is inhibited. In one embodiment, the peptide is selected from a group of peptides including LQG, AQG, LQGV (SEQ ID NO:1 of the hereby incorporated accompanying SEQUENCE LISTING), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVNPVVS (SEQ ID NO:18), LPGC (SEQ ID NO:19), MTRV (SEQ ID NO:20), MTR, and VVC.

The invention is further explained by the use of the following illustrative examples.

EXAMPLES

Ischemia induces increased expression of inflammatory cytokines due to activation of NF-κB and AP-1. Inflammatory cytokines can be expressed by endothelium (for example, by trauma), perivascular cells and adherent or transmigrating leukocytes, inducing numerous pro-inflammatory and pro-coagulant effects. Together these effects predispose to inflammation, thrombosis and hemorrhage. Of clinical and medical interest and value, the present invention provides the opportunity to selectively control NFκB-dependent gene expression in tissues and organs in a living subject, preferably in a primate, allowing up-regulating essentially anti-inflammatory responses such as interleukin (IL) 10, and down-regulating essentially pro-inflammatory responses such as those mediated by tumor necrosis factor α (TNF-α), nitric oxide (NO), IL-5, and IL-1β.

The invention thus provides use of an NFκB-regulating peptide or derivative thereof for the production of a pharmaceutical composition for the treatment of an ischemic event, preferably in a primate, and provides a method of treatment of an ischemic event, notably in a primate. It is preferred that the treatment comprise administering to the subject a pharmaceutical composition comprising an NF-κB-down-regulating peptide or functional analogue thereof. Examples of useful NF-κB-down-regulating peptides are VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGVLPALPQVVC (SEQ ID NO: 17). More down-regulating peptides and functional analogues can be found using the methods as provided herein. Most prominent among NF-κB-down-regulating peptides are VLPALPQVVC (SEQ ID NO:21), LQGVLPALPQ (SEQ ID NO:22), LQG, LQGV (SEQ ID NO:1), and VLPALP (SEQ ID NO:4). These are also capable of reducing production of NO by a cell. It is herein also provided to use a composition that comprises at least two oligopeptides or functional analogues thereof, each capable of reducing production of NO and/or TNF-α by a cell, in particular wherein the at least two oligopeptides are selected from a group including LQGV (SEQ ID NO:1), AQGV (SEQ ID NO:2) and VLPALP (SEQ ID NO:4), for the treatment of an ischemic event and, moreover to treat ischemia—perfusion injury.

In one such instance as provided herein, such a subject has suffered from ischemic events or has undergone anoxia or infarction. A typical clinical instance is the myocardial infarction or chronic myocardial ischemia of heart tissue in various zones or areas of a living human subject or, likewise, a cerebrovascular infarct, such as a sudden massive infarct of the brain with immediate and possibly grave consequences, but also the so-called silent infarcts that go unnoticed for long times but are thought to be involved in the development of certain forms of dementias.

Typical examples also include other cardiovascular or circulatory disorders, such as heart failure, lacunar brain infarctions, Alzheimer's disease, thrombosis, arteriosclerosis, pregnancy-related cardiovascular or circulatory disorders, retinopathies (such as associated with vascular diseases like diabetes) and the like.

In response to a variety of pathophysiological and developmental signals, the NF-κB/Rel family of transcription factors is activated and forms different types of heterodimers and homodimers among themselves to regulate the expression of target genes containing κB-specific binding sites. NF-κB transcription factors are heterodimers or homodimers of a family of related proteins characterized by the Rel homology domain. They form two subfamilies, those containing activation domains (p65-RELA, RELB, and c-REL) and those lacking activation domains (p50, p52). The prototypical NF-κB is a heterodimer of p65 (RELA) and p50 (NF-κB1). Among the activated NF-κB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA-binding sites with varied affinities to different NF-κB dimers have been discovered in the promoters of several eukaryotic genes and the balance between activated NF-κB homodimers and heterodimers ultimately determines the nature and level of gene expression within the cell. The term "NF-κB-regulating peptide" as used herein refers to a peptide or a modification or derivative thereof capable of modulating the activation of members of the NF-κB/Rel family of transcription factors. Activation of NF-κB can lead to enhanced transcription of target genes. Also, it can lead to transcriptional repression of target genes. NF-κB activation can be regulated at multiple levels. For example, the dynamic shuttling of the inactive NF-κB dimers between the cytoplasm and nucleus by IκB proteins and its termination by phosphorylation and proteasomal degradation, direct phosphorylation, acetylation of NF-κB factors, and dynamic reorganization of NF-κB subunits among the activated NF-κB dimers have all been identified as key regulatory steps in NF-κB activation and, consequently, in NF-κB-mediated transcription processes. Thus, an NF-κB-regulating peptide is capable of modulating the transcription of genes that are under the control of the NF-κB/Rel family of transcription factors. Modulating comprises the up-regulation or the down-regulation of transcription. In a preferred embodiment, a peptide according to the invention, or a functional derivative or analogue thereof, is used for the production of a pharmaceutical composition for the treatment of ischemic events. Examples of such events are (but not limited to) cerebral vascular accident (CVA), circulatory diseases of the brain, retinopathies (such as associated with vascular diseases like diabetes), circulatory diseases of pregnancy, thrombosis, atherosclerosis, and so on.

An ischemic event refers to an event in which the blood supply to a tissue is obstructed, such as stroke or myocardial infarction. Due to this obstruction, the endothelial tissue lining the affected blood vessels becomes "sticky" and begins to attract circulating white blood cells. The white cells bound to the endothelium eventually migrate into the brain or cardiac tissue, causing significant tissue destruction. Although neither acute myocardial infarction nor stroke is directly caused by inflammation, much of the underlying pathology and the damage that occurs after an acute ischemic event are caused by acute inflammatory responses during reperfusion, the restoration of blood flow to the affected organ. Thus, a method is provided herein for treating ischemic events, including cerebrovascular disease and ischemic heart failure, comprising administering to a subject in need of such a treatment a peptide according to the invention. In particular, a method is provided to control the acute inflammatory response during reperfusion of the affected body part by administering a peptide, or a modification thereof, capable of modulating expression of a gene encoding a pro-inflammatory cytokine. TNF-α is a pro-inflammatory and multifunctional cytokine that has been implicated in diverse pathological processes such as cancer, infection, and autoimmune inflammation. TNF-α has been recently detected in various cardiac-related illnesses including congestive heart failure, myocarditis, dilated and septic cardiomyopathy, and ischemic heart diseases. TNF mRNA and TNF-α protein were detected in explanted hearts from humans with dilated cardiomyopathy and ischemic heart disease, but TNF-α was not detected in nonfailing myocardium. Although the complete portfolio of signaling pathways that are common to both tumor necrosis factor receptor 1 (TNFR1) and tumor necrosis factor receptor 2 (TNFR2) is not known, it is of interest to note that a recently described zinc finger protein, termed tumor necrosis factor receptor associated factor 2 (TRAF2), has been shown to be involved with both TNFR1- and TNFR2-mediated signaling. Consequently, TRAF2-mediated signaling has been shown to activate NF-κB, with a resultant increase in the expression of the antioxidant protein manganese superoxide dismutase (MSOD). Previous studies suggested that the cytoprotective effects of TNF in the setting of myocardial ischemia were mediated through TNF-induced up-regulation of MSOD. It was suggested that pro-inflammatory cytokines such as TNF may play an important role in the timing of cardiac stress response, both by providing early anti-apoptotic cytoprotective signals that are responsible for delimiting cardiac injury and also by providing delayed signals that facilitate tissue repair and remodeling once myocardial damage has supervened. Given the observation that some peptides according to the invention are capable of up-regulating at least one gene in a cell, the invention now provides a method to increase the expression of gene products such as MSOD and other cytoprotective NF-κB-regulated genes. In particular, the invention provides a method for treating an ischemic-reperfusion injury comprising administering to a subject in need of such treatment a signaling molecule comprising a peptide or functional analogue thereof, the molecule capable of increasing production of IL-10 by a cell. Increased IL-10 production is, for example, achieved by treating the subject systemically or treating the subject's infarcted area locally with peptides AQGV (SEQ ID NO:2), LQGV (SEQ ID NO:1) or VLPALP (SEQ ID NO:4), or a functional analogue thereof similarly capable of modulating translocation and/or activity of a gene transcription factor present in a cell in the ischemic or infracted area. These peptides have the added advantage that TNF-α production by the cell is reduced. When taking ischemic heart failure as an example, an NF-κB-down-regulating peptide according to the invention can, for example, be introduced locally to the infracted area directly as a synthesized compound to living cells and tissues via a range of different delivery means. These include the following:

A. Intracoronary delivery is accomplished using catheter-based deliveries of synthesized peptide (or derivative) suspended in a suitable buffer (such as saline) which can be injected locally (i.e., by injecting into the myocardium through the vessel wall) in the coronary artery using a suitable local delivery catheter such as a 10 mm InfusaSleeve catheter (Local Med, Palo Alto, Calif.) loaded over a 3.0 mm×20 mm angioplasty balloon, delivered over a 0.014 inch angioplasty guide wire. Delivery is typically accomplished by first inflating the angioplasty balloon to 30 psi, and then delivering the protein through the local delivery catheter at 80 psi over 30 seconds (this can be modified to suit the delivery catheter).

B. Intracoronary bolus infusion of a peptide (or derivative) synthesized previously can be accomplished by a manual injection of the substance through an Ultrafuse-X dual lumen catheter (SciMed, Minneapolis, Minn.) or another suitable device into proximal orifices of coronary arteries over 10 minutes.

C. Pericardial delivery of a synthesized peptide (or derivative) is typically accomplished by installation of the peptide-containing solution into the pericardial sac. The pericardium is accessed via a right atrial puncture, transthoracic puncture or a direct surgical approach. Once the access is established, the peptide material is infused into the pericardial cavity and the catheter is withdrawn. Alternatively, the delivery is accomplished via the aid of slow-release polymers such as heparin-alginate or ethylene vinyl acetate (EVAc). In both cases, once the peptide (or derivative) is integrated into the polymer, the desired amount of peptide/polymer is inserted under the epicardial fat or secured to the myocardial surface using, for example, sutures. In addition, the peptide/polymer composition can be positioned along the adventitial surface of coronary vessels.

D. Intramyocardial delivery of synthesized peptide (or derivative) can be accomplished either under direct vision following thoracotomy or using a thoracoscope or via a catheter. In either case, the peptide-containing solution is injected using a syringe or other suitable device directly into the myocardium.

Up to 2 cc of volume can be injected into any given spot and multiple locations (up to 30 injections) can be done in each patient. Catheter-based injections are carried out under fluoroscopic, ultrasound or Biosense NOGA guidance. In all cases, after catheter introduction into the left ventricle, the desired area of the myocardium is injected using a catheter that allows for controlled local delivery of the material. Of course, similar techniques are applied to administer the peptide locally to other infarcted areas, such as seen with cerebrovascular incidents.

In a further embodiment, the invention provides a method for modulating a cerebral ischemic event in a subject comprising providing the subject with a signaling molecule comprising a gene-regulatory peptide or functional analogue thereof in combination therapy with thrombolysis. Two major strategies can be used to reduce the neuronal damage following cerebral ischemia: restoration of cerebral blood perfusion through usage of thrombolytics and inhibition of the apoptotic and inflammatory cascades which result from ischemia through usage of a peptide or functional analogue according to the invention. Combining both treatment strategies provides additional benefits to those achieved by using the individual strategies alone. For instance, restoration of blood flow improves perfusion of the ischemic brain tissue with peptide compositions and enhances their protective effects. Thrombolysis and/or prevention of thrombi are, for example, achieved by intravenous injection of heparin, in a bolus of 5,000 IU, followed by infusion of 15,000 units/hour to induce an APTT-ratio of 2.0. Alternatively, intramuscular injections of low-molecular-weight heparin, such as fragmin of 200 IU/kg/day in two daily doses, are given. Intra-arterial thrombolysis is preferably applied within three hours of onset of ischemic stroke. In short, selective intra-arterial digital subtraction angiography is performed on a biplane, high-resolution angiography system (for example, a Toshiba CAS 500) with a matrix of 1024×1024 pixels. A 5.5.F-JB2 catheter (Valavanis) is inserted in the femoral artery and guided to the cerebral arteries for diagnostic four-vessel angiography. A microcatheter, mostly a Fast Tracker 18 (Target Therapeutics) through the 5.5-F JB2 catheter, is navigated into the cerebral arteria corresponding with the ischemic brain area. A microcatheter is navigated into the occluded cerebral artery. Urokinase (Urokinase HS Medac) in a mean dose usually ranging from 20,000 to 1,250,000 IU is infused directly into or near the proximal end of the occluding thrombus over 60 to 90 minutes. For mechanical disruption and removal of the thrombotic material, additional usage of a very flexible hydrophilic guide wire catheter with a J-shaped tip to avoid perforation of the vessel wall (for example, a Silver Speed MTI 0.008 or 0.010 inch) may be necessary. In addition to agents for thrombolysis and/or prevention of thrombosis, whether applied intravenously, intramuscularly or intra-arterially, treatment with a peptide composition is preferably started at the same time. The invention also provides a method for modulating an ischemic event in a subject comprising providing the subject with a signaling molecule comprising a gene-regulatory peptide or functional analogue thereof for the prevention of cerebral ischemia in patients with defined at-risk periods. Some conditions are frequently followed by cerebral ischemia, in which a peptide or functional analogue thereof is valuable to prevent infarction, illustrated in two specific examples. (1) Cardiac or aortic surgery is frequently complicated with severe hypotensive periods and/or thrombo-embolic events which may result in cerebral or myelum ischemia and infarction. The peptide composition according to the invention can be given in all or a specific subgroup of these patients, before, during and/or after surgery to prevent cerebral ischemia. (2) The final outcome in patients with aneurysmatic subarachnoid hemorrhagia (SAH) is largely determined by the development of cerebral ischemia in the subsequent three weeks. SAH is a life-threatening intracerebral bleeding, usually due to a rupture of an aneurysm of the cerebral arteries in the circulus Willisi. SAH affects 10.5 per 100,000 persons per year of which one-third will die. Up to one-third of the patients will develop cerebral ischemia in the three weeks after SAH, which determines the final outcome and for which all patients with SAH will be admitted to intensive care units. The pathophysiology of cerebral ischemia after SAH is not precisely known, but a specific role is claimed for the presence of subarachnoid blood and/or intracerebral inflammation and vasospasms. Treatment to prevent cerebral ischemia, including triple H-therapy (hypervolemia, hemodilution, hypertension), vasodilators, and endovascular approaches to symptomatic vasospasms, thus far are insufficient in many patients. An NF-κB-down-regulating peptide should be given in this three weeks following SAH, alone or in combination with other forms of preventive treatments, during which these patients are at risk to develop cerebral ischemia and can be monitored at the intensive care unit. In these two and other conditions in which there is a limited period with a significant increase to develop cerebral ischemia, an NF-κB-down-regulating peptide can be used to prevent (further) cerebral ischemia and improve final clinical outcome.

The invention furthermore provides a method to monitor and titrate therapeutic effects of a treatment with a peptide according to the invention in patients with cerebral ischemia. This is foremost achieved by clinical evaluation according to predefined neurological deficit-, disability- and handicap scales, such as the Oxford-handicap scale. CT, CT-angiography, MRI, MR-angiography, and SPECT-scan can be done. Also, cytokines, soluble cytokine-receptors, and chemokines are determined in follow-up plasma and cerebrospinal fluid (CSF) samples. Follow-up CSF samples can be obtained by permanent monitoring via ventricular catheters. Intracerebral HPLC sensors provide for determining parenchyma oxygen, pH and small metabolites including lactate, pyruvate and glucose. This device is already in use in combination with intracranial pressure bolds to monitor the cerebral parenchyma of patients with contusio cerebri.

Preferred routes of administration of a peptide or functional analogue thereof according to the invention in patients with cerebral ischemia are: Intravenously in 0.9% saline solutions according to protocol; intrathecally. In short, the peptide composition may be given after a lumbar puncture with an 18 G needle or after subsequent insertion of an extralumbal catheter with the tip in the intrathecal space. This way of drug administration cannot be used in patients with large infarctions and danger of replacement of brain tissue or herniation, but is a useful way in treating patients with an SAH. Intrathecal drug administration is an established route of drug administration in patients with leukemia and multiple sclerosis. In patients with SAH, extralumar drains are already frequently used to prevent or treat hydrocephalus, a common complication in SAH. Intra-arterial: A similar protocol is used as in intra-arterial thrombolysis. In short, selective intra-arterial digital substraction angiography is performed on a biplane, high-resolution angiography system (for example, a Toshiba CAS 500) with a matrix of 1024×1024 pixels. A 5.5.F-JB2 catheter (Valavanis) is inserted in the femoral artery and guided to the cerebral arteries for diagnostic four-vessel angiography. A microcatheter, mostly a Fast Tracker 18 (Target Therapeutics) through the 5.5-F JB2 catheter, is navigated into the cerebral arteria corresponding with the ischemic brain area. Perfusion of this area with a peptide is achieved according to this protocol. This route of administration is of special interest in the case of combination therapy with intra-arterial thrombolysis. In that case, the same devices and protocols are used in which the microcatheter is navigated into the occluded cerebral artery. Urokinase (Urokinase HS Medac) in a mean dose usually ranging from 20,000 to 1,250,000 IU is infused directly into or near the proximal end of the occluding thrombus over 60 to 90 minutes. For mechanical disruption and removal of the thrombotic material, additional usage of a very flexible hydrophilic guide wire catheter with a J-shaped tip to avoid perforation of the vessel wall (for example, a Silver Speed MTI 0.008 or 0.010 inch) may be necessary. Furthermore, a peptide or functional analogue may be applied locally after craniotomy. A range of suitable pharmaceutical carriers and vehicles is known conventionally to those skilled in the art. Thus, for parenteral or systemic administration, the peptide compound will typically be dissolved or suspended in sterile water or saline. Typically, systemic administration involves intravenous administration, for example, per infusionem. Especially when the subject is at risk to experience iatrogenic reperfusion injury occurring after the ischemic event, for example, due to treatment with an anticoagulant or a thrombolytic agent, systemic administration per infusionem is advantageous, as the risk of bleeding is increased in such patients, necessitating the reduction of invasive measures such as the use of catheters or other puncturing techniques.

Improvement in neurological diseases is limited due to the restricted regeneration capacity of neurons, especially in the central nervous system (CNS). For this reason, and for the high susceptibility of neurons to ischemia and inflammation, treatment strategies in neurology, more than in other medical disciplines, focus on an immediate prevention of (further) neural damage. Ischemia and inflammation of neural tissue are mediated by similar pathogenic pathways leading to and mediated by release and activation of transcription factors, such as NF-κB, and cytokines, such as TNF-α. In addition, in many neurological diseases, both ischemic and inflammatory processes contribute to (further) tissue damage. More than other diseases, neurological disorders will therefore profit from immune-mediating agents, such as by treatment with an β-hCG oligopeptide derivate such as an NF-κB-down-regulating peptide according to the invention, that have an immediate and pleiotropic effect and inhibit these common pathways in both ischemic and inflammatory processes. The invention also provides a method for treating cerebral infarction with an NF-κB-down-regulating peptide according to the invention.

Cerebral infarction is a common and disabling neurological disease which results from an acute onset, insufficient arterial blood supply and ischemia of the associated territorial brain. The causes of the acute insufficient perfusion are (1) thrombo-embolic events related to atherosclerosis of large cerebral arteria and/or cardiac diseases leading to cortical infarctions, (2) hypotension leading to so-called "watershed infarctions," and (3) small vessel diseases related to hypertension and atherosclerosis leading to lacunar infarctions. Each type of infarction may induce distinct patterns of neurological deficits related to the function of the damaged brain area. All these types of infarctions, especially multiple lacunar infarctions, may contribute to the development of vascular (or post-stroke) dementia.

Neurological deficits in stroke are potentially reversible, provided the duration of ischemia is short, such as in "transient ischemic attacks" (TIA's). Partial spontaneous improvement in ischemic strokes most likely results from reversible dysfunction of the penumbra area, where ischemia does not evolve into infarction. The invention also provides treatment of ischemic stroke patients with thrombolytic agents combined with treatment with an NF-κB-down-regulating peptide according to the invention, preferably within three hours after onset of neurological symptoms when cerebral ischemia in potential is a treatable state.

Permanent neurological deficit in stroke patients is due to apoptotic cell death of infarcted brain tissue caused by long-lasting ischemic periods and subsequent activation of apoptotic pathways during the reperfusion phase. Ischemia induces depolarization and release of excitatory amino acids such as glutamate leading to $Ca^{2+}$ and water influx, which successively leads to cerebral edema and $Ca^{2+}$-mediated inflammatory and degenerative processes. Ischemia induces increased expression of TNF and activation of NF-κB. TNF can be expressed by endothelium (for example, by trauma), perivascular cells and adherent or transmigrating leukocytes, inducing numerous pro-inflammatory and procoagulant effects. Together these effects predispose to local inflammation, thrombosis and hemorrhage. As such, they can contribute to stroke initiation, progression of brain damage and development of tolerance to ischemia. In addition, TNF may contribute to repair and recovery after stroke as an important mediator and modulator of inflammation. β-hCG oligopeptide derivates are known to inhibit TNF expression and NF-κB activation and successive inflammatory and apoptotic pathways. These characteristics should enable single β-hCG oligopeptide derivates or cocktails of derivates to prevent the further brain ischemia and infarction and the occurrence of complications, including cerebral edema and secondary hemorrhages, which may contribute to improvement of clinical outcomes in stroke patients. Ischemia and infarction secondary to cerebral contusion and to epi-, subarachnoid- and subdural hemorrhages play a significant role in final brain damage and clinical outcome in patients with these disorders. Local TNF expression and NF-κB activation due to ischemia in these diseases will predispose to local inflammation, thrombosis and hemorrhage, similar to ischemic stroke patients. Therefore, administration of single NF-κB-downregulating peptides or mixtures thereof contributes to improvement of final outcomes also in these diseases. In patients with contusio cerebri and intracranial pressure treatment, it is advantageous to combine treatment with the peptides or functional analogues thereof with osmotic agents like mannitol to reduce intracranial pressure and stimulate cerebral perfusion, i.e., by administering intravenous infusions of mannitol 20% in 0.9% saline solutions of 200 ml, or another hypertonic solution, 1 to 6 times a day. NF-κB-regulating peptides can be given in the same infusion, the peptide (or analogue) concentration preferably being from about 1 to about 1000 mg/L, but the peptide can also been given in a bolus injection. Doses of 1 to 5 mg/kg bodyweight, for example, every eight hours in a bolus injection or per infusionem until the patient stabilizes, are recommended. For example, in cases where large infarcted areas are expected or diagnosed, it is preferred to monitor cytokine profiles, such as TNF-α or IL-10 levels, in the plasma (or cerebrospinal fluid) of the treated patient, and to stop treatment when these levels are normal. In patients with contusio cerebri, intracranial pressure and intraparenchymal oxygen and metabolites can be monitored using intracranial sensors. In a preferred embodiment, the invention provides a method of treating a subject suffering from an ischemic event with a method and signaling molecule according to the invention concomitantly, or at least timely, with a thrombolytic agent, such as (recombinant) tissue plasminogen activator, or truncated forms thereof having tissue plasminogen activity, or streptokinase, or urokinase. In the case of a cerebrovascular incident, such treatment can, for example, take the form of intravenous infusions of recombinant tissue plasminogen activator (rt-PA) at a dose of 0.9 mg/kg (maximum of 90 mg) in 0.9% saline solutions, whereby it is preferred that 10% of the rt-PA dose is given within one to two minutes and the remaining dose of rt-PA in 60 minutes. In the case of an acute myocardial infarction, such treatment can, for example, take the form of intravenous infusions of rt-PA at a dose of 15 mg as an intravenous bolus, followed by 50 mg in the next 30 minutes followed by 35 mg in the next 60 minutes. For the sake of treating the resulting perfusion injury that occurs due to the lysis of the thrombus and the subsequent perfusion of the ischemic area, it is herein provided to also provide the patient with a bolus injection of NF-κB-down-regulating peptide such as AQGV (SEQ ID NO:2), LQGV (SEQ ID NO:1) or VLPALP (SEQ ID NO:4) at 2 mg/kg and continue the infusion with an NF-κB-down-regulating peptide such as AQGV (SEQ ID NO:2), LQGV (SEQ ID NO:1) or VLPALP (SEQ ID NO:4) or a functional analogue thereof at a dose of 1 mg/kg bodyweight for every eight hours. Dosages may be increased or decreased, for example, depending on the outcome of monitoring the cytokine profile in the plasma of the patient. In one embodiment of the present invention, a signal molecule is administered in an effective concentration to an animal or human systemically, e.g., by intravenous, intramuscular or intraperitoneal administration. Another way of administration comprises perfusion of organs or tissue, be it in vivo or ex vivo, with a perfusion fluid comprising a signal molecule according to the invention. Topical administration, e.g., in ointments or sprays, may also apply, e.g., in or around infarcted areas in brain or heart, etc. The administration may be done as a single dose, as a discontinuous sequence of various doses, or continuously for a period of time sufficient to permit substantial modulation of gene expression. In the case of a continuous administration, the duration of the administration may vary depending upon a number of factors which would readily be appreciated by those skilled in the art.

The administration dose of the active molecule may be varied over a fairly broad range. The concentrations of an active molecule which can be administered would be limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

Ten male C57BL/six mice (23 to 26 g), five controls and five test animals, were used as a model for ischemic stroke by middle cerebral artery occlusion/reperfusion. These mice are initially anesthetized with metofane and maintained with i.p. ketamine (60 mg/ml) and xylazine (5 mg/ml). Atropine methyl nitrate (0.18 mg/kg i.p.) is given to prevent airway obstruction. Animals are allowed to breathe spontaneously. A modified intravascular middle cerebral artery (MCA) occlusion technique is used to induce stroke. A nonsiliconized, uncoated 6-0, 8-mm-long prolene suture with a rounded tip (diameter 0.20 mm) is advanced into the internal carotid artery to occlude the MCA for one hour, followed by 24 hours of reperfusion.

Cerebral blood perfusion (CBF) is monitored by laser Doppler flowmetry (Transonic Systems). Laser Doppler flowmetry probes (0.8 mm in diameter) are positioned on the cortical surface 2 mm posterior to the bregma, both 3 and 6 mm to each side of midline. The procedure is considered to be successful if a >85% drop in CBF was observed immediately after placement of the suture.

Survival and neurological deficits are monitored and scored as follows: no neurological deficit (0), failure to extend forepaw fully (1), turning to left (2), circling to left (3), unable to walk spontaneously (4), stroke-related death (5).

Arterial blood gases (pH, $PaO_2$, $PaCO_2$) are measured before and during MCA occlusion with an ABL 30 Acid-Base Analyzer (Radiometer).

Reducing cerebral ischemia by gene-regulatory peptides in murine model.

Each of the five test mice receives a 1:1 mixture of LQGV (SEQ ID NO:1) and VLPALP (SEQ ID NO:4) at 5 mg/kg in a volume of 0.5 ml 0.9% saline which is given intravenously at ten minutes, when blood flow is at a minimum, since these conditions would give a reasonable test of the bioactivity of these peptides during ischemia, because the time course of pathophysiological changes in the present murine model is different from that of human strokes, and the occlusion is experimentally removed after one hour. Each of the control mice receives 0.5 ml 0.9% saline i.v.

Administration of peptides after two to three hours in this murine model would actually be during the reperfusion phase, which may not be fully relevant to the human clinical situation where treatment would be desired within one hour after the stroke, because complete reopening of major occluded blood vessels in humans who experience ischemic stroke might not typically happen spontaneously one hour after the onset of ischemic stroke.

Early results control mice score: 3, 5, 4, 2, 4; test mice score: 3, 1, 3, 2, 1

Possible mechanisms by which peptides reduce cerebral ischemia in a murine model. Not wishing to be bound by theory, the thrombomodulin-protein C (TM-PC) pathway is known to function on endothelium and to counterbalance coagulation. In addition, the TM-PC pathway provides protective signaling that counteracts apoptosis in response to oxygen deprivation. Activated protein C (APC) is a systemic anticoagulant and anti-inflammatory factor which has been demonstrated to protect the brain from ischemic injury. Cytoprotection of brain endothelium by APC in vitro required endothelial protein C receptor (EPCR) and protease-activated receptor-1 (PAR-1), as did in vivo neuroprotective activity in the murine stroke model. It reduces organ damage in animal models of sepsis, ischemic injury and stroke. This invention shows that the above-used gene-regulatory peptides reduce inflammatory mediators, activation of transcription factors, including NF-κB, and directly interfere with the TM-PC pathway. The neuroprotection induced by these peptides is mediated by one or combinations of these effects. Peptides in this way act as a direct cell survival factor and reduce secondary ischemia by their anticoagulant and anti-inflammatory effects.

The peptides as mentioned in this document, such as LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), VVCNYRDVRFE-SIRLPGCPRGVNPVVSYAVALSCQCAL (SEQ ID NO:24), RPRCRPINATLAVEKEGCPVCITVNTTI-CAGYCPT (SEQ ID NO:25), SKAPPPSLPSPSRLPGPS (SEQ ID NO:26), LQGVLPALPQVVC (SEQ ID NO:17), SIRLPGCPRGVNPVVS (SEQ ID NO:27), LPGCPRGVN-PVVS (SEQ ID NO:18), LPGC (SEQ ID NO:19), MTRV (SEQ ID NO:20), MTR, and VVC, were prepared by solid-phase synthesis using the fluorenylmethoxycarbonyl (Fmoc)/tert-butyl-based methodology with 2-chlorotrityl chloride resin as the solid support. The side chain of glutamine was protected with a trityl function. The peptides were synthesized manually. Each coupling consisted of the following steps: (i) removal of the α-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/$H_2O$/triisopropylsilane (TIS) 95:2.5:2.5. After 30 minutes, TIS was added until decolorization. The solution was evaporated in vacuo and the peptide precipitated with diethyl ether. The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/minute; absorbance was detected from 190-370 nm. There were different gradient systems used. For example, for peptides LQG and LQGV (SEQ ID NO:1): ten minutes 100% A followed by linear gradient 0-10% B in 50 minutes. For example, for peptides VLPALP (SEQ ID NO:4) and VLPALPQ (SEQ ID NO:13): five minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The eluant was concentrated and lyophilized in 28 hours. Peptides were prepared for use later by dissolving them in PBS.

RAW264.7 macrophages, obtained from American Type Culture Collection (Manassas, Va.), were cultured at 37° C. in 5% $CO_2$ using DMEM containing 10% FBS and antibiotics (100 U/ml of penicillin and 100 μg/ml streptomycin). Cells ($1 \times 10^6$/ml) were incubated with peptide (10 μg/ml) in a volume of 2 ml. After eight hours of culturing, cells were washed and prepared for nuclear extracts.

Nuclear extracts and Electrophoretic Mobility Shift Assays (EMSA) were prepared according to Schreiber et al., Methods (Schrieber et al., 1989, Nucleic Acids Research 17). Briefly, nuclear extracts from peptide-stimulated or non-stimulated macrophages were prepared by cell lysis followed by nuclear lysis. Cells were then suspended in 400 μl of buffer (10 mM HEPES (pH 7.9), 10 mM KCl, 0.1 mM KCL, 0.1 mM EDTA, 0.1 mM EGTA, 1 mM DTT, 0.5 mM PMSF and protease inhibitors), vigorously vortexed for 15 seconds, left standing at 4° C. for 15 minutes, and centrifuged at 15,000 rpm for two minutes. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 minutes on ice, then the lysates were centrifuged at 15,000 rpm for two minutes. The supernatants containing the solubilized nuclear proteins were stored at −70° C. until used for the (EMSA).

Electrophoretic mobility shift assays were performed by incubating nuclear extracts prepared from control (RAW264.7) and peptide-treated RAW264.7 cells with a 32P-labeled double-stranded probe (5' AGCTCAGAGGGG-GACTTTCCGAGAG 3' (SEQ ID NO:28)) synthesized to represent the NF-κB-binding sequence. Shortly, the probe was end-labeled with T4 polynucleotide kinase according to the manufacturer's instructions (Promega, Madison, Wis.). The annealed probe was incubated with nuclear extracts as follows: in EMSA, binding reaction mixtures (20 μl) contained 0.25 μg of poly(dI-dC) (Amersham Pharmacia Biotech) and 20,000 rpm of 32P-labeled DNA probe in a binding buffer consisting of 5 mM EDTA, 20% Ficoll, 5 mM DTT, 300 mM KCl and 50 mM HEPES. The binding reaction was started by the addition of cell extracts (10 μg) and was continued for 30 minutes at room temperature. The DNA-protein complex was resolved from free oligonucleotide by electrophoresis in a 6% polyacrylamide gel. The gels were dried and exposed to x-ray films.

The transcription factor NF-κB participates in the transcriptional regulation of a variety of genes. Nuclear protein extracts were prepared from LPS- and peptide-treated RAW264.7 cells or from LPS-treated RAW264.7 cells. In order to determine whether the peptide modulates the translocation of NF-κB into the nucleus, EMSA was performed on these extracts. The amount of NF-κB present in the nuclear extracts of RAW264.7 cells were treated with LPS or LPS in combination with a peptide for four hours. Here we determined that, indeed, some peptides are able to modulate the translocation of NF-κB since the amount of labeled oligonucleotide for NF-κB is reduced. In this experiment, peptides that show the modulation of translocation of NF-κB are: VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VLPALPQ (SEQ ID NO:13), GVLPALP (SEQ ID NO:16), VVC, MTRV (SEQ ID NO:20), and MTR.

RAW264.7 mouse macrophages were cultured in DMEM, containing 10% or 2% FBS, penicillin, streptomycin and glutamine, at 37° C., 5% $CO_2$. Cells were seeded in a 12-well plate ($3 \times 10^6$ cells/ml) in a total volume of 1 ml for two hours and then stimulated with LPS (*E. coli* 026:B6; Difco Laboratories, Detroit, Mich., USA) and/or NMPF (1 mg/ml). After 30 minutes of incubation, plates were centrifuged and cells were collected for nuclear extracts. Nuclear extracts and EMSA were prepared according to Schreiber et al. Cells were collected in a tube and centrifuged for five minutes at 2000 rpm (rounds per minute) at 4° C. (Universal 30 RF, Hettich Zentrifuges). The pellet was washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche)) and left on ice for 15 minutes. Twenty-five microliters of 10% NP-40 were added and the sample was centrifuged (two minutes, 4000 rpm, 4° C.). The supernatant (cytoplasmic fraction) was collected and stored at −70° C. The pellet, which contains the nuclei, was washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples were left to shake at 4° C. for at least 60 minutes. Finally, the samples were centrifuged and the supernatant (nucleic fraction) was stored at −70° C.

Bradford reagent (Sigma) was used to determine the final protein concentration in the extracts. For electrophoretic mobility shift assays, an oligonucleotide representing an NF-κB-binding sequence (5'-AGC TCA GAG GGG GAC TTT CCG AGA G-3' (SEQ ID NO:28)) was synthesized. One hundred picomoles of sense and antisense oligo were annealed and labeled with γ-$^{32}$P-dATP using T4 polynucleotide kinase according to the manufacturer's instructions (Promega, Madison, Wis.). Nuclear extract (5-7.5 µg) was incubated for 30 minutes with a 75,000 cpm probe in a binding reaction mixture (20 microliters) containing 0.5 µg poly dI-dC (Amersham Pharmacia Biotech) and binding buffer BSB (25 mM MgCl$_2$, 5 mM CaCl$_2$, 5 mM DTT and 20% Ficoll) at room temperature. The DNA-protein complex was resolved from free oligonucleotide by electrophoresis in a 4-6% polyacrylamide gel (150 V, two to four hours). The gel was then dried and exposed to x-ray film. The transcription factor NF-κB participates in the transcriptional regulation of a variety of genes. Nuclear protein extracts were prepared from either LPS (1 mg/ml), peptide (1 mg/ml) or LPS in combination with peptide-treated and untreated RAW264.7 cells. In order to determine whether the peptides modulate the translocation of NF-κB into the nucleus, EMSA was performed on these extracts. Peptides are able to modulate the basal as well as LPS-induced levels of NF-κB. In this experiment, peptides that show the inhibition of LPS-induced translocation of NF-κB are: VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGVLPALPQVVC (SEQ ID NO:17). Peptides that promote LPS-induced translocation of NF-κB in the experiment are: VLPALPQ (SEQ ID NO:13), GVLPALP (SEQ ID NO:16) and MTRV (SEQ ID NO:20). Basal levels of NF-κB in the nucleus were decreased by VLPALPQVVC (SEQ ID NO:21), LQGVLPALPQ (SEQ ID NO:22), LQG and LQGV (SEQ ID NO:1) while basal levels of NF-κB in the nucleus were increased by GVLPALPQ (SEQ ID NO:23), VLPALPQ, (SEQ ID NO:13) GVLPALP (SEQ ID NO:16), VVC, MTRV (SEQ ID NO:20), MTR and LQGVLPALPQVVC (SEQ ID NO:17). In other experiments, QVVC (SEQ ID NO:29) also showed the modulation of translocation of NF-κB into the nucleus (data not shown).

Further modes of identification of gene-regulatory peptides by NF-κB analysis:

Cells: Cells will be cultured in appropriate culture medium at 37° C., 5% CO$_2$. Cells will be seeded in a 12-well plate (usually $1 \times 10^6$ cells/ml) in a total volume of 1 ml for two hours and then stimulated with a regulatory peptide in the presence or absence of additional stimuli such as LPS. After 30 minutes of incubation, plates will be centrifuged and cells collected for cytosolic or nuclear extracts.

Nuclear Extracts: Nuclear extracts and EMSA could be prepared according to Schreiber et al., Methods (Schreiber et al., 1989, Nucleic Acids Research 17). Cells are collected in a tube and centrifuged for five minutes at 2000 rpm (rounds per minute) at 4° C. (Universal 30 RF, Hettich Zentrifuges). The pellet is washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche)) and left on ice for 15 minutes. Twenty-five microliters of 10% NP-40 is added and the sample is centrifuged (two minutes, 4000 rpm, 4° C.). The supernatant (cytoplasmic fraction) is collected and stored at −70° C. for analysis. The pellet, which contains the nuclei, is washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples are left to shake at 4° C. for at least 60 minutes. Finally, the samples are centrifuged and the supernatant (nucleic fraction) is stored at −70° C. for analysis.

Bradford reagent (Sigma) could be used to determine the final protein concentration in the extracts.

EMSA: For electrophoretic mobility shift assays, an oligonucleotide representing an NF-κB-binding sequence such as (5'-AGC TCA GAG GGG GAC TTT CCG AGA G-3' (SEQ ID NO:28)) is synthesized. One hundred picomoles of sense and antisense oligo are annealed and labeled with γ-$^{32}$P-dATP using T4 polynucleotide kinase according to the manufacturer's instructions (Promega, Madison, Wis.). Cytosolic extract or nuclear extract (5-7.5 µg) from cells treated with regulatory peptide or from untreated cells is incubated for 30 minutes with a 75,000 cpm probe in a binding reaction mixture (20 µl) containing 0.5 µg poly dI-dC (Amersham Pharmacia Biotech) and binding buffer BSB (25 mM MgCl$_2$, 5 mM CaCl$_2$, 5 mM DTT and 20% Ficoll) at room temperature, or cytosolic and nuclear extract from untreated cells or from cells treated with stimuli could also be incubated with a probe in a binding reaction mixture and binding buffer. The DNA-protein complex is resolved from free oligonucleotide by electrophoresis in a 4-6% polyacrylamide gel (150 V, two to four hours). The gel is then dried and exposed to x-ray film. Peptides can be biotinylated and incubated with cells. Cells are then washed with phosphate-buffered saline and harvested in the absence or presence of certain stimulus (LPS, PHA, TPA, anti-CD3, VEGF, TSST-1, VIP or known drugs, etc.). After culturing, cells are lysed and cell lysates (whole lysate, cytosolic fraction or nuclear fraction) containing 200 micrograms of protein are incubated with 50 microliters of Neutr-Avidin-plus beads for one hour at 4° C. with constant shaking. Beads are washed five times with lysis buffer by centrifugation at 6000 rpm for one minute. Proteins are eluted by incubating the beads in 0.05 N NaOH for one minute at room temperature to hydrolyze the protein-peptide linkage and analyzed by SDS-polyacrylamide gel electrophoresis followed by immunoprecipitation with agarose-conjugated anti-NF-κB subunit antibody or immunoprecipitated with antibody against the target to be studied. After hydrolyzing the protein-peptide linkage, the sample could be analyzed by HPLS and mass-spectrometry. Purified NF-κB subunits or cell lysate interaction with biotinylated regulatory peptide can be analyzed on biosensor technology. Peptides can be labeled with FITC and incubated with cells in the absence or presence of different stimulus. After culturing, cells can be analyzed with fluorescent microscopy, confocal microscopy, or flow cytometry (cell membrane staining and/or intracellular staining) or cell lysates are made and analyzed on HPLC and mass-spectrometry. NF-κB-transfected (reporter gene assay) cells and gene array technology can be used to determine the regulatory effects of peptides.

HPLC and mass-spectrometry analysis: Purified NF-κB subunit or cytosolic/nuclear extract is incubated in the absence or presence of (regulatory) peptide, diluted (2:1) with 8 N guanidinium chloride and 0.1% trifluoroacetic acid, injected into a reverse-phase HPLC column (Vydac C18) equilibrated with solvent A (0.1% trifluoroacetic acid), and eluted with a gradient of 0 to 100% eluant B (90% acetonitrile in solvent A). Fractions containing the NF-κB subunit are pooled and concentrated. Fractions are then dissolved in appropriate volume and could be analyzed on mass-spectrometry.

Further references: PCT International Publications WO99/59617, WO97/49721, WO01/10907, and WO01/11048, the contents of the entireties of incorporated herein by this reference.

What is claimed is:

1. A method for modulating an ischemic event in a subject, said method comprising:
providing the subject with a gene-regulatory peptide selected from the group consisting of AQGV (SEQ ID NO: 2), LQGV (SEQ ID NO: 1), VLPALP (SEQ ID NO: 4), and any combination thereof,
thereby modulating the ischemic event in the subject.

2. The method according to claim 1, wherein said gene-regulatory peptide has NF-κB-down-regulating or inhibiting activity in LPS-stimulated RAW264.7 cells.

3. The method according to claim 1, wherein the subject is at risk of experiencing reperfusion injury after said ischemic event.

4. The method according to claim 1, wherein said gene-regulatory peptide has NF-κB-down-regulating or inhibiting activity in LPS unstimulated RAW264.7 cells.

5. The method according to claim 1, further comprising:
providing the subject with a therapeutic amount of a thrombolytic agent.

6. The method according to claim 5, wherein the thrombolytic agent has tissue plasminogen activity.

7. The method of claim 1, wherein providing the subject with a gene-regulatory peptide comprises:
providing the subject with a bolus injection containing the gene-regulatory peptide.

8. The method of claim 7, wherein providing the subject with a gene-regulatory peptide further comprises:
providing the subject with a repeated infusion of the gene-regulatory peptide.

9. A method for treating an ischemic event in a subject, said method comprising:
inhibiting, in the subject, a gene transcription factor comprising an NF-κB/Rel protein by providing the subject with a gene-regulatory peptide selected from the group consisting of AQGV (SEQ ID NO: 2), LQGV (SEQ ID NO: 1), VLPALP (SEQ ID NO: 4), and any combination thereof, so as to down-regulate or inhibit translocation, activity, or translocation and activity of the gene transcription factor, thus treating the subject's ischemic event.

10. A method for modulating an ischemic event in a subject, said method comprising:
administering to the subject a mixture of LQGV (SEQ ID NO:1) and VLPALP (SEQ ID NO:4),
thereby modulating the ischemic event in the subject.

* * * * *